United States Patent
Bell et al.

(10) Patent No.: US 10,420,614 B2
(45) Date of Patent: Sep. 24, 2019

(54) X-RAY SCALING DEVICES, SYSTEMS, AND METHODS

(71) Applicant: Zimmer, Inc., Warsaw, IN (US)

(72) Inventors: Tyler Bell, Warsaw, IN (US); James Grimm, Winona Lake, IN (US); Greg Mangan, Warsaw, IN (US)

(73) Assignee: Zimmer, Inc., Warsaw, IN (US)

(*) Notice: Subject to any disclaimer, the term of this patent is extended or adjusted under 35 U.S.C. 154(b) by 89 days.

(21) Appl. No.: 15/607,213

(22) Filed: May 26, 2017

(65) Prior Publication Data

US 2017/0340391 A1 Nov. 30, 2017

Related U.S. Application Data

(60) Provisional application No. 62/342,527, filed on May 27, 2016.

(51) Int. Cl.
*A61B 17/58* (2006.01)
*A61B 17/60* (2006.01)
(Continued)

(52) U.S. Cl.
CPC ............ *A61B 34/10* (2016.02); *A61B 5/1075* (2013.01); *A61B 6/04* (2013.01); *A61B 6/0492* (2013.01); *A61B 6/505* (2013.01); *A61B 6/583* (2013.01); *A61B 90/39* (2016.02); *A61B 6/12* (2013.01); *A61B 2017/0092* (2013.01); *A61B 2034/108* (2016.02); *A61B 2090/061* (2016.02); *A61B 2090/364* (2016.02); *A61B 2090/3916* (2016.02); *A61B 2090/3966* (2016.02); *A61B 2090/3991* (2016.02)

(58) Field of Classification Search
CPC combination set(s) only.
See application file for complete search history.

(56) References Cited

U.S. PATENT DOCUMENTS

| 4,915,112 A | 4/1990 | Singer |
| 2004/0086082 A1* | 5/2004 | Foos ................ A61B 5/1072 378/163 |
| 2013/0266124 A1 | 10/2013 | Coursolle |

FOREIGN PATENT DOCUMENTS

| FR | 2913592 | 9/2008 |
| WO | 2017205817 | 11/2017 |

OTHER PUBLICATIONS

"International Application Serial No. PCT/US2017/034812, International Search Report dated Aug. 8, 2017", 4 pgs.
(Continued)

*Primary Examiner* — Sameh R Boles
(74) *Attorney, Agent, or Firm* — Schwegman Lundberg & Woessner, P.A.

(57) ABSTRACT

Various systems, devices, and methods for facilitating efficient anatomical registration in surgical navigation are disclosed. Such systems and devices can have a data collection unit and a scaling device. The scaling device has a main body having an anatomical registration feature defined therein and at least one scaling marker pathway that is selectively oriented with respect to the anatomical registration feature to facilitate repeatable gross placement of a scaling marker relative to a selected anatomical feature. The scaling marker is selectively displaceable along a scaling marker pathway about and between a first end and a second end thereof to fine-tune scaling marker placement prior to image capture.

20 Claims, 5 Drawing Sheets

(51) Int. Cl.
*A61F 2/00* (2006.01)
*A61B 34/10* (2016.01)
*A61B 6/04* (2006.01)
*A61B 6/00* (2006.01)
*A61B 90/00* (2016.01)
*A61B 5/107* (2006.01)
*A61B 6/12* (2006.01)
*A61B 17/00* (2006.01)

(56) References Cited

OTHER PUBLICATIONS

"International Application Serial No. PCT/US2017/034812, Written Opinion dated Aug. 8, 2017", 6 pgs.

* cited by examiner

X-RAY SCALING DEVICES, SYSTEMS, AND METHODS

CLAIM OF PRIORITY

This application claims the benefit of priority to U.S. Provisional Application No. 62/342,527, filed May 27, 2016, which is incorporated herein by reference in its entirety.

FIELD

The present disclosure relates to X-ray scaling devices, systems, and associated methods.

BACKGROUND

This section provides background information related to the present disclosure, which is not necessarily prior art.

Orthopedic digital templating enables healthcare professionals to determine the correct size of a prosthesis to be used for a patient prior to surgery. Digital templating yields the best sizing accuracy if scaling devices are used within the x-ray image. A scaling device includes a scaling marker that has a known geometry and is visible in a radiographic image. The marker is used by digital templating software to accurately scale the image. However, users can compromise the image scaling of the software due to improper scaling marker placement.

SUMMARY

This section provides a general summary of the disclosure, and is not a comprehensive disclosure of its full scope or all of its features.

The present inventors have recognized that improper placement and, additionally or alternatively, variability of placement of a scaling marker can compromise the accuracy of image scaling in orthopedic digital templating. Devices, systems, and methods for facilitating consistent and proper scaling marker placement would therefore be desirable. Accordingly, the present teachings provide for devices, systems, and methods for consistent and proper scaling marker placement. The device can comprise a main body having at least one anatomical registration feature defined therein. The main body can further comprise a scaling marker pathway. The scaling marker pathway can be selectively oriented with respect to the anatomical registration feature and can facilitate repeatable gross placement of a scaling marker relative to the selected anatomical feature. The scaling marker pathway can have a first end and an opposed second end. The scaling marker can be selectively displaceable along the scaling marker pathway about and between the first end and the second end to enable fine placement of the scaling marker relative to the selected anatomical structure.

The present teachings also provide for a method for imaging a selected anatomy comprising the steps of: securing the main body with respect to an anatomical registration feature; adjusting a scaling marker about and between a first end and a second end of a scaling marker pathway to fine-tune placement of the scaling marker relative to the selected anatomy; and capturing and scaling an image of the selected anatomy.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The present teachings provide for devices, systems, and methods for consistent and proper scaling marker placement. Such systems, devices, and methods can facilitate consistent placement of a scaling marker relative to an anatomical structure, thereby reducing or eliminating image scaling error introduced through variability of scaling marker placement. Additionally or alternatively, such systems, devices and methods can provide for proper scaling marker placement relative to an anatomical structure for a given image, thereby reducing or eliminating image scaling error due to improper scaling marker placement.

Figure 1:
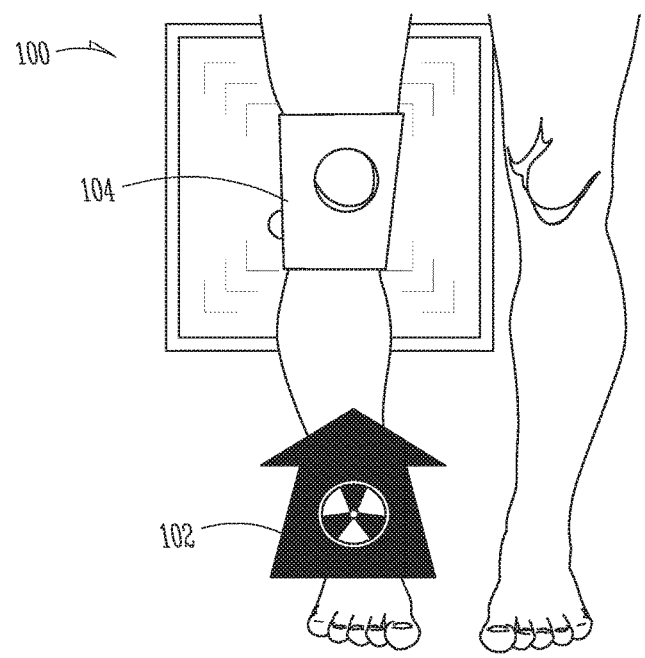
FIG. 1 illustrates an anatomical registration system in accordance with at least one example of the present disclosure.

With initial reference to FIG. 1, a system 100 comprises a data collection unit 102 and a scaling device 104. The data collection unit 102 and scaling device 104 of the present teachings can be used in combination for anatomical registration prior to and/or during a surgical procedure.

Figure 2:
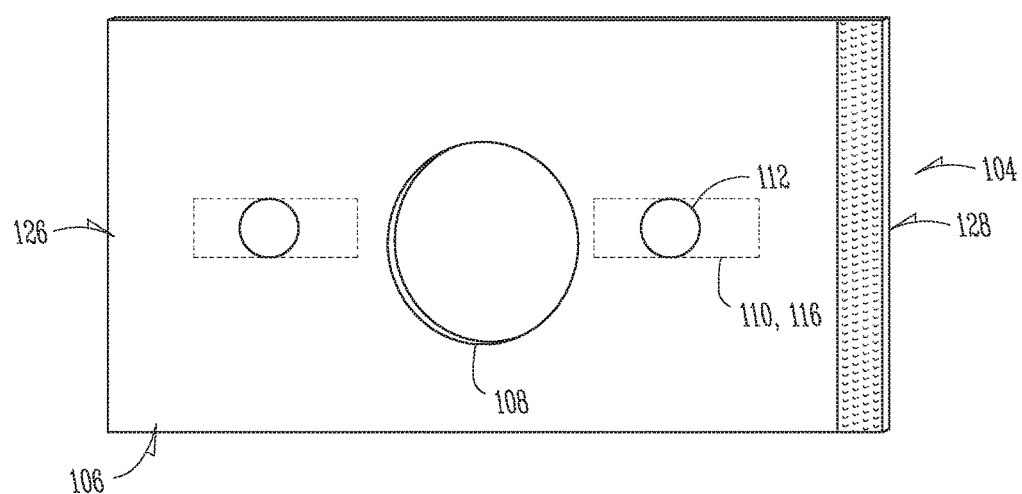
FIG. 2 illustrates one example of a scaling device.

In one aspect illustrated in FIG. 2, the scaling device 104 can comprise a main body 106 having an anatomical registration feature 108 defined therein. The main body can further comprise a scaling marker pathway 110. The scaling marker pathway 110 can be selectively oriented with respect to the anatomical registration feature 108 and can facilitate repeatable gross placement of a scaling marker 112 relative to the selected anatomical feature. The scaling marker pathway 110 can have a first end and an opposed second end. The scaling marker 112 can be selectively displaceable along the scaling marker pathway 110 about and between the first end and the second end to enable fine placement of the scaling marker 112 relative to the selected anatomical structure. The main body 106 can be substantially radiolucent. The scaling marker 112 can be substantially radiolucent and, additionally or alternatively, can be a sphere. In operation, the main body 106 of the scaling device 104 can be positioned on a patient such that the anatomical registration feature 108 can be aligned with a selected anatomical feature, facilitating gross placement of the scaling marker 112 relative to the selected anatomical structure. An operator can then selectively displace the scaling marker 112 along the scaling marker pathway 110 about and between the first end and the second end so that the position of the scaling marker 112 can be fine-tuned prior to image capture by the data collection unit 102.

In one aspect illustrated in FIG. 2, the scaling marker pathway 110 can comprise a pocket 116. The pocket 116 can be disposed in and/or on the main body 106. In an additional or alternative aspect illustrated in FIG. 3, the scaling marker pathway 110 can comprise a pocket 116 that can be offset from the main body 106. The scaling marker 112 can be disposed in the pocket 116 and the scaling marker 112 can be selectively displaceable about and between the first end and the second end of the pocket 116.

In another aspect, the scaling device 104 can further comprise a scaling marker enclosure 118. The scaling marker pathway 110 can comprise a first side of a fastener 120 such as, for example and without limitation, a hook-and-loop type fastener, snaps, buttons, or any other suitable fastener known in the art. The scaling marker enclosure 118 can further comprise a second, mating side of the fastener 120. In operation, an operator can adjust the location of the scaling marker enclosure 118 along the scaling marker pathway 110 to fine-tune placement of the scaling marker 112 prior to image capture by the data collection unit 102. In another aspect, the main body 106 can comprise a plurality of scaling marker pathways 110, each of the plurality of scaling marker pathways 110 corresponding to scaling marker placement for a selected image of the selected anatomical structure. In operation, an operator can selectively position the scaling marker enclosure 118 along a selected scaling marker pathway 110 corresponding to a selected image to be captured by the data collection unit 102.

Figure 4:
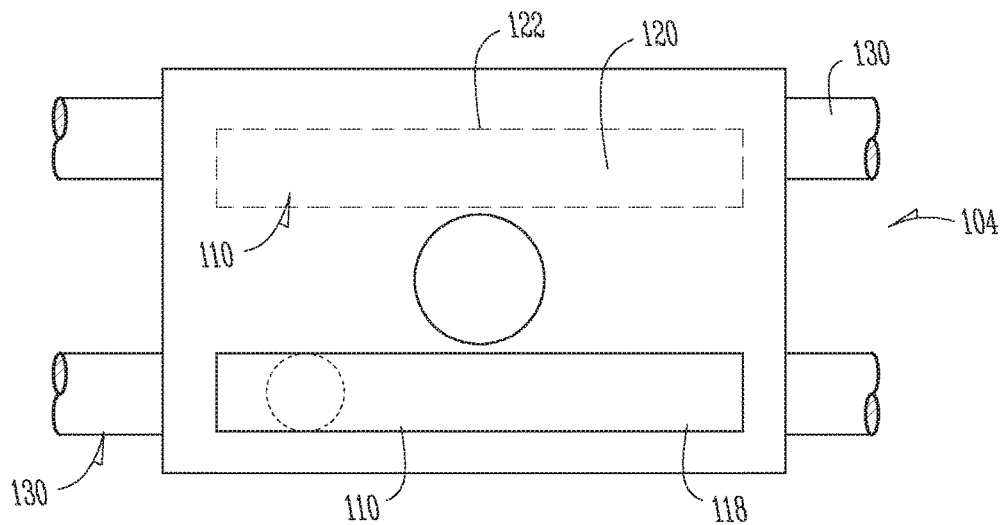
FIG. 4 illustrates another example of a scaling device.

In another aspect illustrated in FIG. 4, the scaling marker enclosure 118 can contain a scaling marker 112. The scaling marker 112 can be selectively displaceable about and between the first end and the second end of the scaling marker enclosure 118. The scaling marker pathway 110 can comprise a slot 122 defined in the main body 106. The scaling marker enclosure 118 can have a complementary geometry to and can be receivable in the slot 122. In another aspect, the main body 106 can comprise a plurality of slots 122, each of the plurality of slots 122 corresponding to scaling marker placement for a selected image of the selected anatomical structure. In operation, an operator can position the scaling marker enclosure 118 in a selected slot 122 corresponding to scaling marker placement for a selected image to be captured by the data collection unit 102.

In one aspect, the main body 106 can comprise a sleeve 124. The sleeve can be adapted to receive the selected anatomical structure. Optionally, the sleeve can be a compression sleeve. In one aspect, the scaling device 104 can comprise a sleeve 124 and the anatomical registering feature 108 can comprise a hole disposed in the sleeve. In one illustrative example, the selected anatomical structure can comprise a knee and the anatomical registering feature 108 can comprise a hole for receiving a patella.

In another aspect, the main body 106 can comprise a first end 126 and an opposed second end 128 that can be secured together with a fastener. Optionally, the main body 106 can further comprise a strap 130 coupled to and extending away from the first end 126 and a loop 132 coupled to the second end 128. The strap 130 can comprise a hook-and-loop fastener or any other suitable fastener type. In operation, the first strap 130 can be passed through the loop 132 and folded back on itself to bring the hook-and-loop fastener into mating contact and secure the main body to the selected anatomical structure. In one illustrative example, the selected anatomical structure can comprise a knee and the anatomical registering feature 108 can comprise a hole for receiving the patella.

Figure 3:
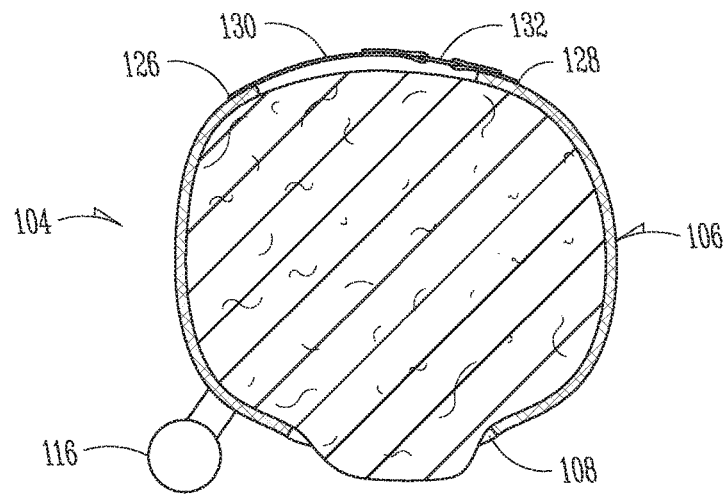
FIG. 3 illustrates another example of a scaling device.

In other aspects illustrated in at least FIGS. 2-4, the scaling device 104 can accommodate variations in either or both of leg size and diameter. In additional or alternative aspects illustrated in at least FIGS. 2-4, a single scaling device 104 can be used for scaling a variety of different images, such as both femur and tibia images, and images on both the left and right legs.

Figure 5:
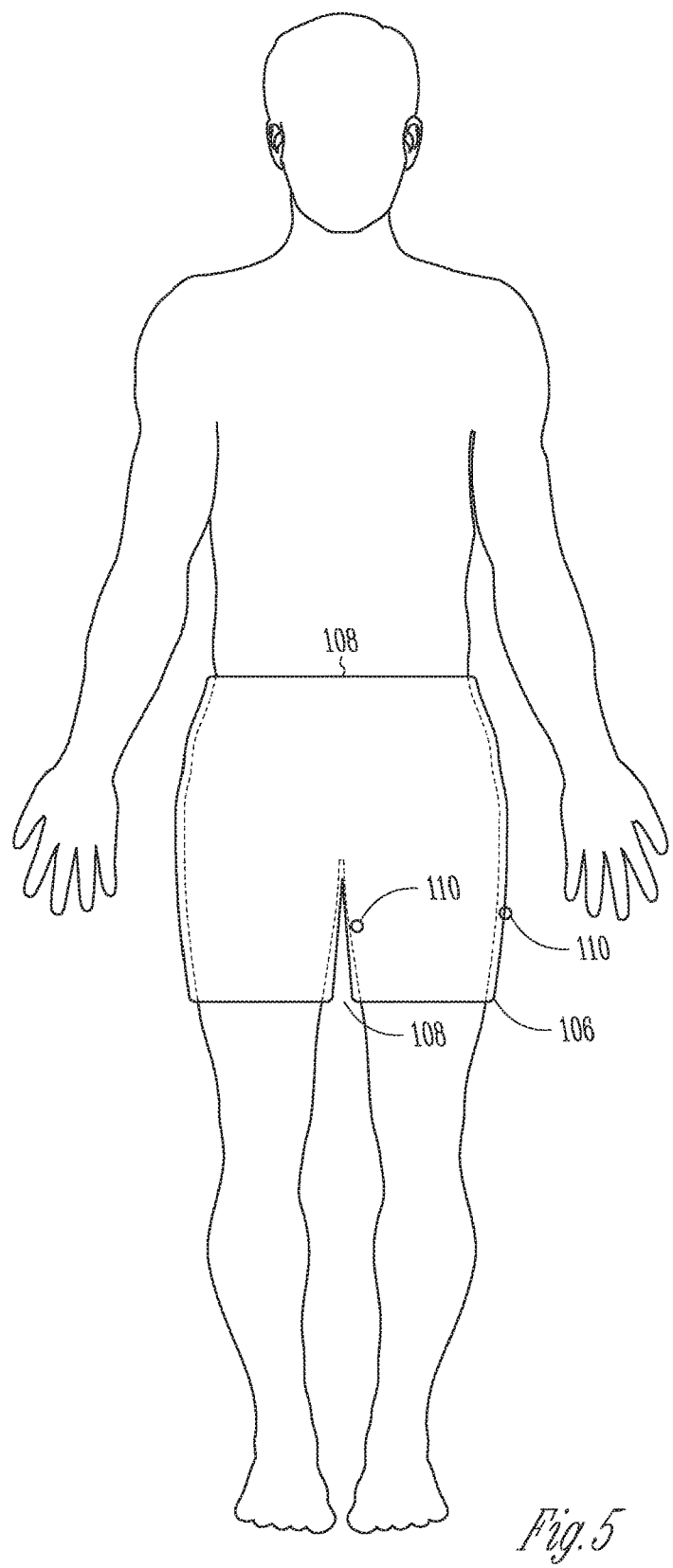
FIG. 5 illustrates another example of a scaling device.

In another aspect illustrated in FIG. 5, the main body 106 can comprise a pair of shorts or pants, wherein at least one of the waist and the split of the legs of the pair of shorts or pants comprises the anatomical registering feature 108. The scaling marker pathways 110 can be selectively arranged for one or more of pelvic imaging, hip imaging, femoral imaging, and the like. In one aspect, the shorts or pants can be reversible so that one device can accommodate both the left and right side anatomy of a patient.

Figure 6:
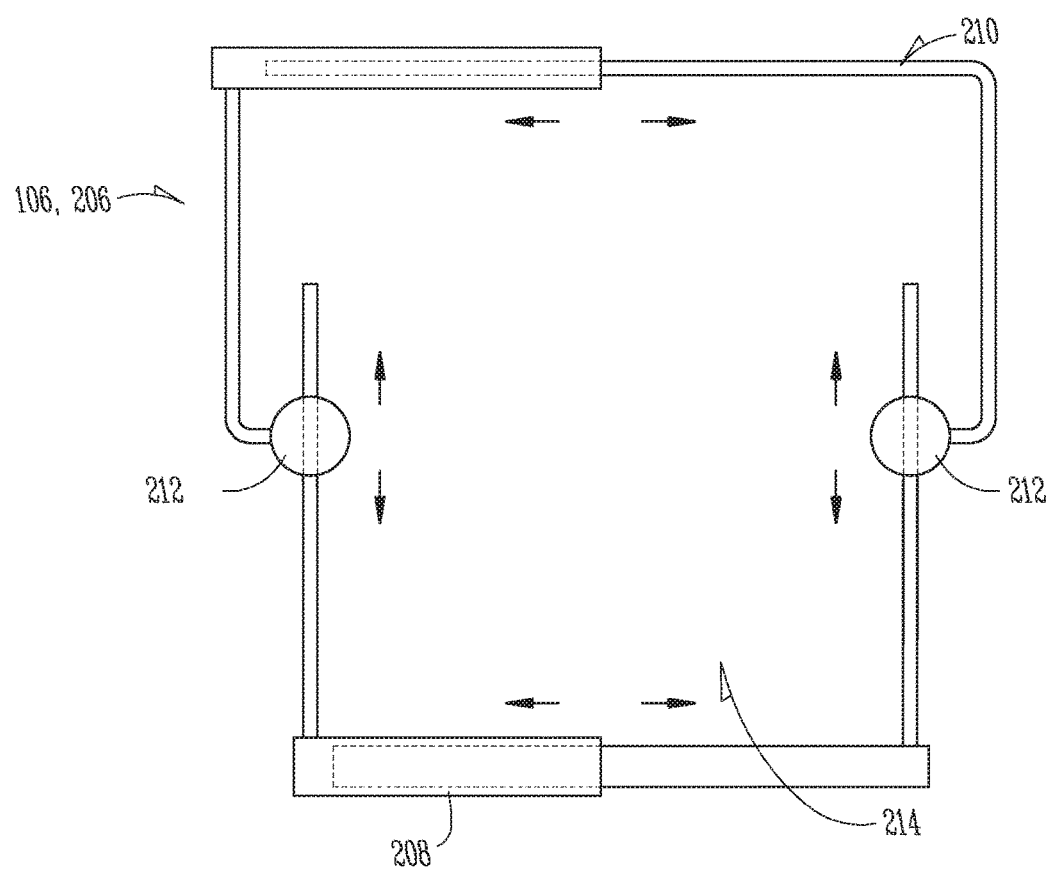
FIG. 6 illustrates another example of a scaling device.

In another aspect illustrated in FIG. 6, the main body 106 can comprise an adjustable enclosure 206 comprising a base plate member 208, a handle member 210, and two (or more) scaling markers 212 coupled to at least the handle member 210. The anatomical registering feature can be a hole 214 defined by the adjustable enclosure 206 for receiving a leg of a patient. At least the base plate member 208 can be laterally expandable to accommodate various patient leg widths. The handle member 210 can be slidingly engaged with the base plate member 208 and selectively adjustable about and between a first position where the handle member 210 is located a first distance from the base plate member 208 and a second position where the handle member 210 is located a second, greater distance from the base plate member 208. The pathway traveled by the handle member 210 between the first position and the second position can define the scaling marker pathway 110. The scaling markers 212 can each move with the handle member 210 such that they can be fixed relative to each other as the handle member 210 moves about and between the first position and second position. The adjustable enclosure can comprise a radiolucent material. The adjustable enclosure 206 can have a free state where the base plate member 208, the handle member 210, and the scaling markers 112 can be static and an engaged state where the handle member 210 and scaling markers 212 can move relative to the base plate member 208.

Figure 7:
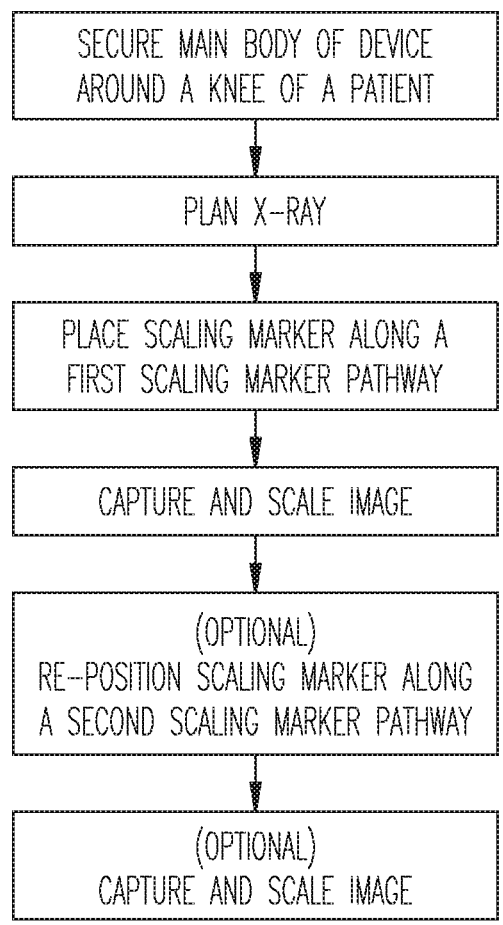
FIG. 7 is a flow chart illustrating a process of anatomical registration in accordance with at least one example of the present disclosure.

In other aspects illustrated in FIG. 7, the present teachings provide for a method for imaging a selected anatomy comprising the steps of: securing the main body with respect to an anatomical registration feature; adjusting a scaling marker about and between a first end and a second end of a scaling marker pathway to fine-tune placement of the scaling marker relative to the selected anatomy; and capturing and scaling an image of the selected anatomy. In one illustrative example, the device shown in any one of FIGS. 2-4 can be used according to the following exemplary method to obtain images of a knee prior to surgery. The main body 106 can be secured around the leg of a patient such that anatomical registering feature 108 receives the patella. A lateral X-ray can be planned and the scaling marker 112 can be placed along a first scaling marker pathway 110a on the main body corresponding to the anterior side of the knee, ensuring the resulting image will not have the scaling marker 112 obscuring important anatomical features of the knee. The data collection unit 102 can then capture the lateral image of the knee with the scaling marker 112 and use the scaling marker characteristics to scale the image. Optionally, the scaling marker 112 can then be removed from the first scaling marker pathway 110a and placed on a second scaling marker pathway 110b corresponding to the lateral side of the knee, again ensuring the scaling marker 112 will not obscure important anatomical features of the knee. Again, the data collection unit 102 can capture the lateral image of the knee with the scaling marker 112 and use the scaling marker characteristics to scale the image. Some numbered examples of the present subject matter are listed below:

Example 1 is a scaling device that can comprise a main body having at least one anatomical registering feature defined therein, wherein the main body can be conformable to a selected anatomical structure, wherein the main body can further comprise a scaling marker pathway that can be selectively oriented with respect to the anatomical registering feature and can facilitate repeatable gross placement of a scaling marker relative to the selected anatomical structure, wherein the scaling marker pathway can have a first end and an opposed second end, and wherein the scaling marker can be selectively displaceable along the scaling marker pathway about and between the first end and the second end to enable fine placement of the scaling marker relative to the selected anatomical structure.

In Example 2, the subject matter of Example 1 can optionally be configured such that the scaling marker pathway comprises a pocket.

In Example 3, the subject matter of Example 2 can optionally be configured such that the pocket can be disposed in the main body.

In Example 4, the subject matter of any one or more of Examples 2-3 can optionally be configured such that the pocket can be offset from the main body.

In Example 5, the subject matter of any one or more of Examples 2-4 can optionally be configured such that the scaling marker can be disposed in the pocket.

In Example 6, the subject matter of any one or more of Examples 1-5 can optionally be configured such that the scaling device can further comprise a scaling marker enclosure.

In Example 7, the subject matter of Example 6 can optionally be configured such that the scaling marker pathway can comprise one side of a hook and loop type fastener and wherein the scaling marker enclosure can further comprise a mating second side of a hook and loop type fastener.

In Example 8, the subject matter of any one or more of Examples 6-7 can optionally be configured such that the scaling marker pathway can comprise a slot defined in the main body, wherein the scaling marker enclosure can have a complementary geometry to and can be receivable in the slot.

In Example 9, the subject matter of any one or more of Examples 1-8 can optionally be configured such that the scaling marker can be a sphere.

In Example 10, the subject matter of any one or more of Examples 1-9 can optionally be configured such that the main body can comprise a sleeve.

In Example 11, the subject matter of Example can optionally be configured such that the sleeve can be a compression sleeve.

In Example 12, the subject matter of any one or more of Examples 1-11 can optionally be configured such that the main body can comprise a first end and an opposed second end, wherein the first and second ends can be secured together with a fastener.

In Example 13, the subject matter of Example 12 can optionally be configured such that the main body can comprise a first strap extending from the first end and a second strap extending from a second end, wherein the first strap can comprise a hook and loop fastener, wherein the second strap can comprise a loop, and wherein, in operation, the first strap can be passed through the loop and folded back on itself to engage the hook and loop fastener and secure the main body to the selected anatomical structure.

In Example 14, the subject matter of any one or more of Examples 1-13 can optionally be configured such that the selected anatomical structure can comprise a knee.

In Example 15, the subject matter of Example 14 can optionally be configured such that the anatomical registering feature can comprise a hole disposed in the main body for receiving a patella.

In Example 16, the subject matter of any one or more of Examples 1-15 can optionally be configured such that the main body can be radiolucent.

In Example 17, the subject matter of any one or more of Examples 1-16 can optionally be configured such that the selected anatomical structure can comprise at least one of a pelvis, a hip, and a femur.

In Example 18, the subject matter of Example 17 can optionally be configured such that the anatomical registering feature can comprise at least one of a waist and a split of the legs of a pair of shorts.

In Example 19, the subject matter of any one or more of Examples 1-18 can optionally be configured such that the main body can comprise an adjustable enclosure that can comprise a handle member that can be selectively slidingly engaged with a base plate member.

In Example 20, the subject matter of Example 19 can optionally be configured such that the handle member can be selectively moveable about and between a first position where the handle member is located a first distance from the base plate member and a second position where the handle member is located a second, greater distance from the base plate member.

In Example 21, the subject matter of any one or more of Examples 19-20 can optionally further comprise a plurality of scaling markers that can be fixed to at least the handle member, wherein the plurality of scaling markers do not move relative to each other as the handle member moves about and between the first position and the second position.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A scaling device, comprising:
a main body having at least one anatomical registering feature defined therein, wherein the main body is conformable to a selected anatomical structure, wherein the main body further comprises a scaling marker pathway that is selectively oriented with respect to the anatomical registering feature at a fixed distance and facilitates repeatable gross placement of a scaling marker relative to the selected anatomical structure, wherein the scaling marker pathway has a first end and an opposed second end, and wherein the scaling marker is selectively displaceable along the scaling marker pathway about and between the first end and the second end to enable fine placement of the scaling marker relative to the selected anatomical structure along a fixed path less than an overall length of the main body.

2. The scaling device of claim 1, wherein the scaling marker pathway comprises a pocket disposed in the main body and the scaling marker is disposed in the pocket.

3. The scaling device of claim 2, wherein the pocket is disposed in the main body.

4. The scaling device of claim 2, wherein the pocket is offset from the main body.

5. The scaling device of claim 1, wherein the scaling device further comprises a scaling marker enclosure.

6. The scaling device of claim 5, wherein the scaling marker pathway comprises one side of a hook and loop type fastener and wherein the scaling marker enclosure further comprises a mating second side of a hook and loop type fastener.

7. The scaling device of claim 5, wherein the scaling marker pathway comprises a slot defined in the main body, wherein the scaling marker enclosure has a complementary geometry to and is receivable in the slot.

8. The scaling device of claim 1, wherein the scaling marker is a sphere.

9. The scaling device of claim 1, wherein the main body comprises a compression sleeve.

10. The scaling device of claim 1, wherein the main body comprises a first end and an opposed second end, wherein the first and second ends can be secured together with a fastener.

11. The scaling device of claim 10, wherein the main body comprises a first strap extending from the first end and a second strap extending from a second end, wherein the first strap comprises a hook and loop fastener, wherein the second strap comprises a loop, and wherein, in operation, the first strap is passed through the loop and folded back on itself to engage the hook and loop fastener and secure the main body to the selected anatomical structure.

12. The scaling device of claim 1, wherein the selected anatomical structure comprises a knee and the anatomical registering feature comprises a hole disposed in the main body for receiving a patella.

13. The scaling device of claim 1, wherein the main body is radiolucent.

14. The scaling device of claim 1, wherein the selected anatomical structure comprises at least one of a pelvis, a hip, and a femur and the anatomical registering feature comprises at least one of a waist and a split of the legs of a pair of shorts.

15. The scaling device of claim 1, wherein the main body comprises an adjustable enclosure comprising a handle member that is selectively slidingly engaged with a base plate member.

16. The scaling device of claim 15, wherein the handle member is selectively moveable about and between a first position where the handle member is located a first distance from the base plate member and a second position where the handle member is located a second, greater distance from the base plate member.

17. The scaling device of claim 16, further comprising a plurality of scaling markers fixed to at least the handle member, wherein the plurality of scaling markers do not move relative to each other as the handle member moves about and between the first position and the second position.

18. A scaling device, comprising:
a scaling marker;
a main body extending from a first end to a second end and being stretchable to surround and conform to an anatomical structure of a knee, the main body comprising:
an anatomical registering feature comprising a hole extending through the main body for receiving a patella; and
a scaling marker pathway disposed in the main body at a fixed distance from the anatomical registration feature, the scaling marker pathway extending from a third end to a fourth end to extend across a medial or lateral side of the anatomical structure of the knee; and
a closure mechanism for attaching the first and second ends of the main body at a posterior side of the anatomical structure of the knee;
wherein the scaling marker is selectively displaceable along the scaling marker pathway between the first end and the second end.

19. The scaling device of claim 18, wherein the first end is displaced from the second end along a first axis and the third end is displaced from the fourth end along a second axis, the first axis and the second axis being parallel to each other.

20. The scaling device of claim 18, wherein the main body extends over a first length between the first end and the second end and the scaling marker pathway extends over a second length between the third end and the fourth end, the second length being less than the first length.

* * * * *